US009279134B2

(12) United States Patent
Leonetti et al.

(10) Patent No.: US 9,279,134 B2
(45) Date of Patent: Mar. 8, 2016

(54) METHODS FOR ISOLATING BACTERIA

(71) Applicants: DEINOVE, Paris (FR); CENTRE NATIONAL DE LA RECHERCHE SCIENTIFIQUE, Paris (FR)

(72) Inventors: Jean-Paul Leonetti, Montpellier (FR); Stéphanie Texier, Montauban (FR)

(73) Assignees: DEINOVE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/030,504

(22) Filed: Sep. 18, 2013

(65) Prior Publication Data

US 2014/0017724 A1 Jan. 16, 2014

Related U.S. Application Data

(63) Continuation-in-part of application No. 13/145,246, filed as application No. PCT/EP2010/050513 on Jan. 18, 2010, now Pat. No. 9,005,954.

(60) Provisional application No. 61/145,606, filed on Jan. 19, 2009.

(30) Foreign Application Priority Data

Jan. 19, 2009 (EP) .................................. 09305041

(51) Int. Cl.
*A61K 38/00* (2006.01)
*C12N 1/00* (2006.01)
(Continued)

(52) U.S. Cl.
CPC .................. *C12P 1/04* (2013.01); *A23L 1/0345* (2013.01); *A23L 1/30* (2013.01); *A23L 1/3014* (2013.01);
(Continued)

(58) Field of Classification Search
CPC ........ A61K 35/74; A61K 38/00; A01N 63/00; C12P 21/02
USPC ........................................ 424/93.4; 435/71.3
See application file for complete search history.

(56) References Cited

U.S. PATENT DOCUMENTS 3,716,453 A 2/1973 Okumura et al.
4,975,365 A 12/1990 Grossman et al.
(Continued)

FOREIGN PATENT DOCUMENTS

CN 1563407 A * 3/2004 .............. C12P 23/00
EP 263684 * 4/1988 .............. A61K 7/42
(Continued)

OTHER PUBLICATIONS

Hughs, CC et al, 2008, Organic Letters, pp. 629-631, vol. 10(4).*
(Continued)

*Primary Examiner* — Albert Navarro
*Assistant Examiner* — Ginny Portner
(74) *Attorney, Agent, or Firm* — Saliwanchik, Lloyd & Eisenschenk

(57) ABSTRACT

The present invention relates to compositions and methods to identify novel bacteria and metabolites derived therefrom. More specifically, the invention describes a novel method to isolate bacteria producing metabolites of interest from environmental samples. Particularly, the invention discloses a method to select rare antibiotic producing bacteria. The invention can be used from any sample and allows the isolation of bacteria having e.g., pharmaceutical or agrochemical interest.

8 Claims, 1 Drawing Sheet

Figure 1A:
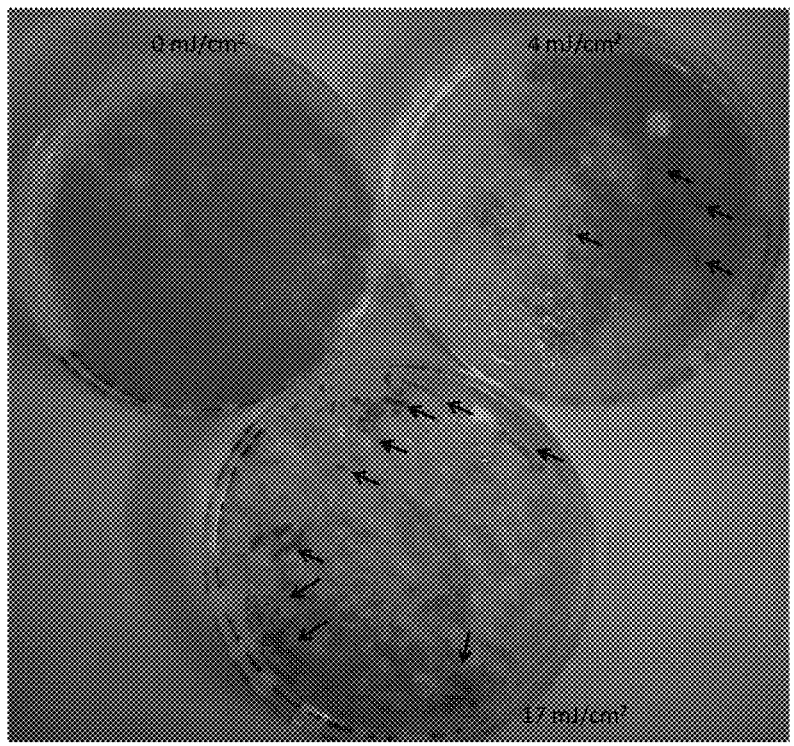

(51) Int. Cl.

| | |
|---|---|
| C12P 1/04 | (2006.01) |
| C12P 23/00 | (2006.01) |
| C12R 1/01 | (2006.01) |
| A23L 1/30 | (2006.01) |
| C07G 11/00 | (2006.01) |
| C12Q 1/02 | (2006.01) |
| A23L 1/03 | (2006.01) |
| A61K 35/741 | (2015.01) |
| C12N 1/20 | (2006.01) |

(52) U.S. Cl.
CPC ............. *A61K 35/741* (2013.01); *C07G 11/00* (2013.01); *C12N 1/20* (2013.01); *C12P 23/00* (2013.01); *C12Q 1/025* (2013.01); *C12R 1/01* (2013.01)

(56) References Cited

U.S. PATENT DOCUMENTS

| | | | |
|---|---|---|---|
| 5,447,856 A * | 9/1995 | Kizawa et al. | 435/100 |
| 5,821,088 A * | 10/1998 | Darzins et al. | 435/69.7 |
| 6,102,690 A | 8/2000 | Ingram et al. | |
| 6,150,392 A | 11/2000 | Thomas et al. | |
| 6,183,736 B1 * | 2/2001 | Moyne et al. | 424/93.462 |
| 6,384,013 B1 * | 5/2002 | Burkhardt et al. | 530/317 |
| 6,410,305 B1 * | 6/2002 | Miller et al. | 435/268 |
| 6,984,523 B2 * | 1/2006 | Cheng et al. | 435/410 |
| 7,034,140 B2 * | 4/2006 | Bramucci et al. | 536/23.7 |
| 7,063,955 B2 * | 6/2006 | Cheng et al. | 435/67 |
| 7,074,588 B2 * | 7/2006 | Cheng et al. | 435/67 |
| 7,217,537 B2 * | 5/2007 | Miller et al. | 435/41 |
| 7,235,170 B2 * | 6/2007 | Watanabe et al. | 205/777.5 |
| 7,759,057 B2 | 7/2010 | Zhou et al. | |
| 2003/0143660 A1 * | 7/2003 | Cheng et al. | 435/67 |
| 2003/0143707 A1 | 7/2003 | Narumi et al. | |
| 2003/0170847 A1 * | 9/2003 | Bramucci et al. | 435/193 |
| 2003/0175841 A1 * | 9/2003 | Watanabe et al. | 435/14 |
| 2003/0182687 A1 * | 9/2003 | Cheng et al. | 800/282 |
| 2003/0203476 A1 | 10/2003 | Fliermans | |
| 2004/0146966 A1 * | 7/2004 | Cheng et al. | 435/67 |
| 2004/0219629 A1 * | 11/2004 | Cheng et al. | 435/67 |
| 2005/0221466 A1 * | 10/2005 | Liao et al. | 435/252.3 |
| 2006/0141558 A1 * | 6/2006 | Tang et al. | 435/67 |
| 2007/0031951 A1 * | 2/2007 | Huang et al. | 435/156 |
| 2008/0003640 A1 * | 1/2008 | Hsu et al. | 435/69.1 |
| 2009/0093015 A1 * | 4/2009 | Louie et al. | 435/67 |
| 2009/0227029 A1 * | 9/2009 | Radman et al. | 435/441 |
| 2011/0104766 A1 | 5/2011 | Leonetti et al. | |
| 2011/0306085 A1 | 12/2011 | Isop et al. | |
| 2012/0052540 A1 | 3/2012 | Biton et al. | |
| 2012/0058533 A1 | 3/2012 | Biton et al. | |
| 2012/0264179 A1 * | 10/2012 | Burgard et al. | 435/121 |
| 2013/0337485 A1 * | 12/2013 | Mrak et al. | 435/26 |

FOREIGN PATENT DOCUMENTS

| | | | |
|---|---|---|---|
| EP | 2218773 | 8/2010 | |
| KR | 10-2004-0107942 | * 12/2004 | A61K 7/48 |
| KR | 100836093 | 6/2008 | |
| WO | WO 95/27064 | 10/1995 | |
| WO | WO 97/10352 | 3/1997 | |
| WO | WO 01/23526 | 4/2001 | |
| WO | WO 02/059351 | 8/2002 | |
| WO | 2005/062867 | * 7/2005 | |
| WO | WO 2006/131734 | 12/2006 | |
| WO | WO 2007/128338 | 11/2007 | |
| WO | WO 2009/063079 | 5/2009 | |
| WO | WO 2010/094665 | 8/2010 | |
| WO | WO 2010/130806 | 11/2010 | |
| WO | WO 2010/130812 | 11/2010 | |
| WO | WO2011/107506 | 9/2011 | |

OTHER PUBLICATIONS

Asker, D et al, Appl. Microbiol. Biotechnol. 2007, vol. 77, pp. 383-392.*

Macherla, V. R. et al, Journal of Natural Products, 2007, vol. 70, pagtes 1454-1457.*

Sarkar, Sovan et al, The Journal of Biologial Chemistry, vol. 282, No. 8, pp. 5641-5652, Feb. 23, 2007, Trehalose, A Novel mTOR independent Autophagy Enhander, Accelerates the Clearance of Mutant Huntingtin and alpha-Synuclein.*

Sarkar, S et al, The Journal of Biological Chemistry, vol. 282(8), pp. 5641-5652, Feb. 23, 2007, Trehalose, a Novel mTOR independent Autophagy Enhancer Accelerates the Clearance of Mutant Huntingtin and Alpha-Synuclein.*

Hirsch, P et al, System Appl. Microbiol., vol. 27, p. 636-645, 2004, Deinococcus frigens sp. nov., Deinococcus saxicola sp. nov., and Deinococcus marmoris sp. nov., Low temperature, and Draught tolerating US resistant Bacteria from Continental Antarctica.*

Rajpurohit, YS et al, Journal of Bacteriology, Jun. 2008, 3948-3954, vol. 190(11), Involvement of a Protein Kinase Activity Inducer in DNA Double Strand Break Repair and Radioresistance of Deinococcus radiodurans.*

Misra, HS et al, FEBS Letters, vol. 578, pp. 26-30, 2000 Pyrroloquinoline-quinone: a reactive oxygen species scavenger in bacteria.* van Kleef et al, FEBS, vol. 237(No. 1,2) pp. 91-97, Sep. 1988, L-Tyrosin is the precursor of PQQ biosynthesis in Hyophomicrobium X.*

McArthur, KA et al, J. Nat. Prod., 2008, vol. 71, pp. 1732-1737, Lynamicins A-E, chlorinated Bisindole Pyrrole Antibiotics from a Novel Marine Actinomycete.*

Lemee, L et al, Tetrahedron, vol. 53(3), pp. 919-926, 1997, Deinoxanthin: A New Carotenoid Isolated from Deinococcus radiodurans.*

Shukla, Manish et al, Current Microbiology, vol. 54, pp. 142-148, 2007, Multiple Stress Tolerance of Ionizing Radiation Resistant Bacterial Isolates Obtained from Various Habitats: Correlation Between Stresses.*

Tian, B et al, Biochimica et Biophysica Acta, vol. 1770, 2007, pp. 902-911, Evaluation of the antioxidant effects of carotenoids from Deinococcus radiodurans through targeted mutagenesis, chemiluminescence, and DNA damage analysis.*

Kota, S et al, PprA: A protein implicated in radioresistance of Deinococcus radiodurans stimulates catalase activity in *Escherichia coli*, Applied Microbiology and Biotechnology, vol. 72, 2006, pp. 790-796.*

Debbab, A et al, Minireview: Bioactive Compounds from Marine Bacteria and Fungi, Microbial Biotechnology, 2010, vol. 3(5), pp. 544-563.*

Hughes, Chambers C et al, The Marinopyrroles, Antibiotics of an Unprecedented Structure Class from a Marine Streptomyces sp. Org. Lett., Feb. 21, 2008, vol. 10(4), pp. 1-9.*

Fenical, W. et al, Developing a new resource for drug discovery: marine actinomycete bacteria, Nature Chemical Biology, vol. 2,(12), pp. 666-673.*

Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.

Alea, F. et al. "Selection of hypercellulolytic derepressed mutants of *Cellulomonas* sp." *Applied Microbiology and Biotechnology*, 1991, pp. 643-645, vol. 35, No. 5.

Temp, U. et al. "A Small-Scale Method for Screening of Lignin-Degrading Microorganisms" *Applied Environmental Microbiology*, Apr. 1998, pp. 1548-1549, vol. 64, No. 4.

Zenoff, V. F. et al. "Diverse UV-B Resistance of Culturable Bacterial Community from High-Altitude Wetland Water" *Current Microbiology*, May 1, 2006, pp. 359-362, vol. 52, No. 5.

Pavlikova, E. et al. "Improvement of the Basidiomycete *Coprinus* sp." *Folia Microbiologica*, Jan. 1, 1982, pp. 126-130, vol. 27, No. 2.

Written Opinion in International Application No. PCT/EP2010/051885, Aug. 23, 2010, pp. 1-10.

Omelchenko, M. et al. "Comparative genomics of *Thermus thermophilus* and *Deinococcus radiodurans*: divergent routes of adaptation to thermophily and radiation resistance" *BMC Evolutionary Biology*, 2005, pp. 1-22, vol. 5, No. 57.

(56) References Cited

OTHER PUBLICATIONS

Weisburg, W.G. at al. "The *Deinococcus-Thermus* Phylum and the Effect of rRNA Composition on Phylogenetic Tree Construction" *Systematic and Applied Microbiology*, 1989, pp. 128-134, vol. 11.
Database EMBL, Accession No. M21413, "D. radiodurans 16s ribosomal RNA gene" XP002633260, Nov. 23, 1989, p. 1.
Suihko, M.L. et al. "Characterization of aerobic bacterial and fungal microbiota on surfaces of historic Scottish monuments" *Systematic and Applied Microbiology*, 2007, pp. 494-508, vol. 30.
Database EMBL, Accession No. EF093134, "*Deinococcus sp.* VTT E-052909 16S ribosomal RNA gene, complete sequence" XP002633261, Aug. 7, 2007, pp. 1-2.
Database EMBL, Accession No. AM283039, "*Deinococcus sp.* Han23 partial 16S rRNA gene, strain Han23" XP002633262, Jun. 26, 2006, p. 1.
Rainey, F. et al. "Phylogenetic Diversity of the Deinococci as Determined by 16S Ribosmal DNA Sequence Comparison" *International Journal of Systemic Bacteriology*, Apr. 1997, pp. 510-514, vol. 47, No. 2.
Written Opinion in International Application No. PCT/EP2011/053089, Mar. 2, 2010, pp. 1-7.
Brim, H. et al. "Engineering *Deinococcus radiodurans* for metal remediation in radioactive mixed waste environments" *Nature Biotechnology*, Jan. 2000, pp. 85-90, vol. 18, XP-002491111.
Henstra, A. M. et al. "Microbiology of synthesis gas fermentation for biofuel production" *Current Opinion in Biotechnology*, 2007, pp. 200-206, vol. 18, XP-22110181.
John, R. P. et al. "Fermentative production of lactic acid from biomass: an overview on process developments and future perspectives" *Appl. Microbio. Biotechnol.*, 2007, pp. 524-534, vol. 74, XP-002464997.
Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.
Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.
Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.
Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.
Smith, M. D. et al. "Gene expression in *Deinococcus radiodurans*" *Gene*, 1991, pp. 45-52, vol. 98, XP-002938523.
Zahradka, K. et al. "Reassembly of shattered chromosomes in *Deinococcus radiodurans*" *Nature*, Oct. 5, 2006, pp. 569-573, vol. 443, XP-002491114.
Office Action dated Nov. 8, 2012 in U.S. Appl. No. 12/740,404.
Fontaine, L. et al. "Molecular Characterization and Transcriptional Analysis of *adhE2*, the Gene Encoding the NADH-Dependent Aldehyde/Alcohol Dehydrogenase Responsible for Butanol Production in Alcohologenic Cultures of *Clostridium acetobutylicum* ATCC 824" *Journal of Bacteriology*, Feb. 2002, pp. 821-830, vol. 184, No. 3.
Skory, C. D. "Isolation and Expression of Lactate Dehydrogenase Genese from *Rhizopus oryzae*" *Applied and Environmental Microbiology*, Jun. 2000, pp. 2343-2348, vol. 66, No. 6.
Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.

Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.
Anonymous. "Conference de presse: Preséntation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10, XP-002591932.
Written Opinion in International Application No. PCT/EP2010/056592, Jul. 29, 2010, pp. 1-7.
Kolari, M. et al. "Colored moderately thermophilic bacteria in paper-machine biofilms" *Journal of Industrial Microbiology and Biotechnology*, Apr. 2003, pp. 225-238, vol. 30, No. 4.
Written Opinion in International Application No. PCT/EP2010/056600, May 14, 2009, pp. 1-8.
Ferreira, A. et al. "*Deinococcus geothermalis* sp. nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4.
Weon, H. et al. "*Deinococcus cellulosilyticus* sp. nov., isolated from air" *International Journal of Systematic and Evolutionary Microbiology*, Aug. 1, 2007, pp. 1685-1688, vol. 57, No. Part 8.
Written Opinion in International Application No. PCT/EP2008/065613, Jan. 28, 2009, pp. 1-8.
Berdy, J. "Bioactive Microbial Metabolites—A personal view" *Journal of Antibiotics*, Jan. 1, 2005, pp. 1-26, vol. 58, No. 1.
Singh, S. et al. "Biodiversity, chemical diversity and drug discovery" *Progress in Drug Research*, 2008, pp. 142-174, vol. 65.
Rainey, F. et al. "Extensive Diversity of Ionizing-Radiation-Resistant Bacteria Recovered from Sonoran Desert Soil and Description of Nine New Species of the Genus *Deinococcus* Obtained from a Single Soil Sample" *Applied and Environmental Microbiology*, Sep. 2005, pp. 5225-5235, vol. 71, No. 9.
Yang, B. et al. "Effects of microwave irradiation on isolation of soil actinomycetes" *Yingyong Shengtai Xuebao*, May 2008, pp. 1091-1098, vol. 19, No. 5.
Sinha, R. et al. "UV-protectants in cyanobacteria" *Plant Science*, Dec. 23, 2007, pp. 278-289, vol. 174, No. 3.
Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.
Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.
Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.
Keller, M. et al. "Tapping Into Microbial Diversity" *Nature Reviews*, Feb. 2004, pp. 141-150, vol. 2, No. 2.
Makarova, K. et al. "Genome of the Extremely Radiation-Resistant Bacterium *Deinococcus radiodurans* Viewed from the Perspective of Comparative Genomics" *Microbiology and Molecular Biology Reviews*, Mar. 2001, pp. 44-79, vol. 65, No. 1.
Reichenbach, H. "Myxobacteria, producers of novel bioactive substances" *Journal of Industrial Microbiology & Biotechnology*, Jan. 1, 2001, pp. 149-156, vol. 27. No. 3.
Bibb, M. "Regulation of secondary metabolism in streptomycetes" *Current Opinion in Microbiology*, 2005, pp. 208-215, vol. 8, No. 2.
Written Opinion in International Application No. PCT/EP2010/050513, Apr. 24, 2010, pp. 1-10.
Narumi, I., "Practical application of high-efficiency DNA repair reagents using radioresistant bacterial protein" Atomic Energy eye, *Information Journal of Atomic Energy General Sciences* (Gensiryoku Sogokagaku Jyohoshi), 2006, pp. 60-63, vol. 52 No. 6, Nikkan Kygyo Shuppan Production, Ryouich Kanno.
"Radioresistant Bacteria Confoundedly Strong Toward Ultraviolet Rays," *Japan Atomic Energy Research Institute*, 2003, p. 39.

\* cited by examiner

METHODS FOR ISOLATING BACTERIA

The present invention relates to compositions and methods to identify novel bacteria and metabolites derived therefrom. More specifically, the invention describes a novel method to isolate bacteria producing metabolites of interest from environmental samples. Particularly, the invention discloses a method to select novel antibiotic producing bacteria. The invention can be used from any sample and allows the isolation of bacteria having e.g., pharmaceutical or agrochemical interest.

BACKGROUND

For time immemorial, mankind has sourced surrounding organisms for therapeutic purposes, and most of the commercial antibiotics still have a natural origin. During the last 10 years, in an effort to rationalize and to speed up antibacterial discovery processes, the industry has moved from natural products and a molecule-oriented discovery strategy to synthetic molecules and a target-oriented strategy.

After years of uniformization of antibiotic R&D process, with an unprecedented high attrition rate, it is necessary to return to natural resources. Indeed, the screening of natural product libraries usually yields a higher percentage of antibiotics hits than that of chemical libraries, and consequently provides a higher probability to obtain a therapeutic. The first reason probably lies in the ecologic role of the antibiotics, which have been optimized through the course of evolution, to defend plants, animals and micro-organisms against other living organisms. Furthermore, natural products are generally as lipophilic as combinatorial compounds, but they have an unparalleled structural diversity and dispersion in chemical space. This helps to find rare hydrophilic hits which can be optimized for in vivo applications.

It is generally assumed that 20 to 30 percent of the bacteria isolated from environmental sources such as soil or water are antibiotics producers (Bérdy, 2005). For obvious reasons, the fitter and the most represented bacteria are the most frequently isolated. This explains why many antibiotics produced by Bacillus or Pseudomonas have already been documented, and why it is more and more difficult to find new molecular entities produced by these genera. Other families of under-represented bacteria, more adapted to antibiotic production, due to a bigger genome, can be easily isolated with adapted techniques. This is the case of actinomycetals, by far the best antibiotic producers (Bérdy, 2005). They were extensively studied by the pharmaceutical industry between 1950 and 1980, and it is now difficult to identify strains producing non-redundant molecules.

In the last decade, efforts have been devoted to isolating rare bacteria in order to find new chemical entities of pharmaceutical interest. Myxobacteria, for example, are known since the 1940's, but due to difficulties encountered for isolating them, they were under-represented in the collections. Thanks to an extensive collection campaign carried out by Reichenbach H and collaborators, so far about 80 different compounds and 450 structural variants produced by Myxobacteria have been characterized (Reichenbach, 2001). Many of those compounds were new. Among them is the antineoplasic drug, epothilones, currently being evaluated in clinical trials.

It is generally recognized, however, that microbiologists are unable to culture most soil microorganisms (Schoenborn et al., 2005). The number of cultivable cells in soil is often only about 1% of the total number of cells present. Most of these bacteria are difficult to detect and isolate using standard isolation techniques, either because they are rare in the environment, or because they are less adapted to environmental conditions than other bacteria like Pseudomonas spp. or Bacillus spp. and are rapidly overgrown. Several isolation techniques aiming to increase the diversity of the isolates have been published. For example, serial liquid dilution culture has been used successfully to improve cultivability (Schoenborn et al., 2005) and to facilitate the isolation of bacteria from diverse environments. Yang et al., 2008, also described the use of microwave treatment to isolate rare actinomycetes. WO02/059351 concerns a method for enriching a microbial population from a natural environment using e.g., hot spring water.

However, environmental microorganisms still represent a rich and unexploited resource of novel compounds and activities, and there is a need in the art for improved or alternative methods to identify bacteria of interest.

SUMMARY OF THE INVENTION

The present application provides a novel approach to identify or isolate bacteria from environmental samples. More particularly, the invention discloses an efficient and rapid method of identifying or isolating rare bacteria from environmental samples using a DNA damaging treatment.

An object of the present invention therefore resides in a method to identify or isolate a (secondary) metabolite producing bacterium, the method comprising subjecting a sample comprising uncharacterized bacteria to a cell destructing DNA damaging treatment and identifying or isolating from said treated sample a bacterium which produces the (secondary) metabolite. In a preferred embodiment, the treatment is a repeated irradiation treatment.

In this respect, a particular object of this invention is a method to identify or isolate a metabolite-producing bacterium, the method comprising:

a) providing a sample comprising uncharacterized bacteria;

b) subjecting the sample to a repeated irradiation treatment;

c) identifying or isolating a living or growing bacterium from said treated sample; and d) selecting a bacterium of step c) which produces the metabolite.

In a particular embodiment, the treatment comprises a sequential UV treatment, e.g., a repetition of at least 2, preferably 3 or more irradiations at essentially regular intervals.

In a particular embodiment, the treatment comprises a repeated UV irradiation.

According to another particular embodiment, the invention relates to a method to identify or isolate a metabolite-producing bacterium, the method comprising:

a) providing a sample comprising uncharacterized bacteria;

b) adding to the sample an antibiotic of the bleomycin family;

c) identifying or isolating a living or growing bacterium from said treated sample; and d) selecting a bacterium of step c) which produces the metabolite.

The preferred antibiotic of the bleomycin family is bleocin.

The metabolite may be any pharmaceutical product, such as antibiotics, bacteriostatic compounds, anti-metabolite agents, chemotherapeutic compounds, anti-fungal agents, anti-viral compounds, cytokine-activity compounds or cell-growth factors.

Another object of this invention is a method to identify or isolate a bacterium which produces an antibiotic or a bacteriostatic-compound, the method comprising:

a) providing a sample comprising uncharacterized bacteria;

b) subjecting the sample to a repeated irradiation treatment, preferably a repeated UV treatment;

c) identifying or isolating living or growing bacteria from said treated sample; and d) exposing identified or isolated bacteria of step c), or an extract thereof, to a reference bacterial strain and identifying or isolating a bacterium which exhibits an antibiotic or bacteriostatic activity.

In a preferred embodiment, the methods of the present invention comprise a further step of isolating or purifying the metabolite produced by said bacterium.

Furthermore, the methods of the invention optionally comprise a further step of modifying, either genetically, biologically or chemically, the identified or isolated bacteria or their DNA by any technical process known per se by a skilled person, said modification aiming to improve e.g., the viability, growth or function of the said bacteria, e.g., in order to improve the antibiotic activity or production. This includes, without limitation, cell fusion, accelerated evolution, DNA shuffling technologies, insertion of eukaryote, prokaryote or synthetic nucleic acid (e.g., DNA) from another strain, or any genetic engineering technology. Said modification step can be carried out on the isolated bacteria, or at any earlier stage of the process, e.g., on the sample of step a), for instance.

Another object of this invention resides in a wild type or modified bacterium obtained by a method as disclosed above, or an extract thereof.

A further object of this invention is a method of producing a metabolite, particularly a pharmaceutical compound, the method comprising (i) identifying or isolating a bacterium which produces said metabolite using the method as defined above and (ii) producing said antibiotic.

A further object of this invention is a method of identifying, isolating or producing a pharmaceutical compound (such as an antibiotic), using a wild type or modified *Deinococcus* bacterial strain.

A further object of this invention resides in the use of a wild type or modified *Deinococcus bacterium* to produce a pharmaceutical compound (such as an antibiotic).

A further object of this invention is an antibiotic derived from a wild type or modified *Deinococcus* bacteria.

A further object of this invention is a method of producing a recombinant host cell, the method comprising identifying or isolating a bacterium according to the method as defined above and cloning one or several genes (or corresponding synthetic or recombinant nucleic acids) from said bacterium in another host cell, thereby producing a recombinant host cell.

The methods of the present invention can be used with various samples, such as environmental samples, and has been used successfully to isolate novel bacteria having advantageous pharmaceutical and/or agro-chemical properties.

LEGEND TO THE FIGURES

FIG. 1: Bacterial mat obtained after: a) 1 exposure to UV: 0, 4 and 17 $mJ/cm^2$ and b) repeated exposures to UV treatment of 4 $mJ/cm^2$. Dark colonies are *D. radiopugnans*. The other bacteria belong to soil community.

DETAILED DESCRIPTION OF THE INVENTION

The present application describes a novel method to identify or isolate bacteria from samples. More particularly, the invention discloses an efficient and rapid method of identifying or isolating rare bacteria from environmental samples using a cell destructing DNA damaging treatment. The invention further relates to methods of producing pharmaceutical compounds using such bacteria.

Isolation and Culture of Bacteria

Resistance of bacteria to UV or radiation has been extensively studied to understand how bacteria can survive in such aggressive environment (Makarova et al., 2001). Rainey et al., 2005, showed that *Geodermatophylus* spp. and *Deinococcus* spp. are among the most radiation-resistant bacteria collected from the Sonoran desert soils. Other bacteria were also isolated namely, *Deinococcus, Hymenobacter, Kineococcus, Kocuria,* and *Methylobacterium*.

The present invention now proposes the use of a cell destructing DNA damaging treatment to isolate novel (under-represented) bacteria producing metabolites. The present invention indeed shows that such a treatment, which would normally cause substantial cell death, unexpectedly allows the selection of under-represented bacteria having remarkable properties of producing valuable metabolites.

The invention now shows for the first time that, after a cell destructing DNA damaging treatment, it is possible to isolate a high number of bacteria able to produce valuable secondary metabolites.

An object of the present invention therefore resides in a method to identify or isolate a metabolite producing bacterium, the method comprising subjecting a sample comprising uncharacterized bacteria to a cell destructing DNA damaging treatment and identifying or isolating from said treated sample a bacterium which produces the metabolite.

In a particular embodiment, the method comprises:

a) providing a sample comprising uncharacterized bacteria;

b) subjecting the sample to a cell destructing DNA damaging treatment;

c) identifying or isolating a living or growing bacterium from said treated sample; and d) selecting a bacterium of step c) producing the metabolite.

The method can be implemented with various samples comprising uncharacterized bacteria, particularly with samples which are or derive from an environmental sample. Within the context of this invention, environmental samples include any sample containing (a plurality of) uncharacterized (micro)organisms, particularly uncultivated microorganisms (e.g., microorganisms that have not been purposely cultured and expanded in isolated form). The sample may be obtained or derived from natural environments or from artificial or specifically created environments.

As indicated, the sample may be any environmental sample, such as those obtained or derived from soil, water, vegetal extract, biological material, sediments, peatlands, industrial effluents or sites, mineral extracts, sand, and the like. The sample may be collected from various regions or conditions, such as but not limited to tropical regions, volcanic regions, forests, farms, industrial areas, etc. The sample usually contains various species of (uncharacterized, uncultivated) microorganisms, such as terrestrial microorganisms, marine microorganisms, freshwater microorganisms, symbiotic microorganisms, etc. Species of such environmental microorganisms include bacteria, algae, fungi, yeasts, molds, viruses, etc. The microorganisms may include extremophile organisms, such as e.g., thermophiles. The sample typically comprises various species of such (uncultivated) microorganisms, as well as various amounts thereof. Furthermore, the sample may contain, in addition, known and/or cultivable microorganisms (e.g., prokaryotic or eukaryotic).

It should be understood that the present invention is not limited to any specific type of sample or environmental microorganism, but can be implemented using any sample comprising uncultivated microorganisms.

In a preferred embodiment, the sample is or derives from soil, water, hot springs, marine environment, mud, wood, stone, moss, vegetal extract, lichen, biological material, sediment, biofilm, industrial effluents, gas, sand, oil, sewage, or animal or human dejection.

For use in the present invention, the sample may be wet, soluble, dry, in the form of a suspension, paste, etc. Furthermore, prior to step b) of the method, the sample may be treated to improve the process, for instance to enrich for microorganisms, e.g., such as through filtration, washings, concentration, dilution, steering, drying, etc.

In a particular embodiment, the sample is in the form of a filtered suspension. More particularly, the sample may be sterile-filtered and/or placed in sterile water, prior to treatment step b).

Step b) of the process comprises subjecting the sample (i.e., microorganisms contained in the sample) to a cell destructing DNA damaging treatment.

The cell destructing DNA damaging treatment designates a treatment that causes substantial cell death in the sample, as opposed to mere mutagenic treatments which introduce DNA modifications. In particular, the cell destructing DNA damaging treatment is a treatment that is sufficient to cause 90% cell death, or more, in a culture of *E. coli* bacteria. Even more preferably, the cell destructing DNA damaging treatment is a treatment that is sufficient to reduce by at least 2 log the bacterial titer in a culture of *E. coli*. Surprisingly, the invention shows that such a treatment, which would normally be lethal to most cell populations, allows the efficient and rapid isolation of novel microorganisms from various types of samples, which microorganisms produce valuable (secondary) metabolites. This result is particularly surprising since subjecting microorganisms to such cell destructing DNA damaging treatment would have been expected to prevent isolation of living microorganisms. Surprisingly, the invention allows the selection of rare microorganisms from the sample, especially microorganisms having the ability to either reassemble their genome or to resist DNA damage.

The invention thus discloses, for the first time, the use of a cell destructing DNA damaging treatment to select, with a high efficacy, under-represented bacteria producing valuable (secondary) metabolites. As illustrated in the examples, the invention allowed the isolation of novel bacterial strains of *Deinococcus* sp, *Bacillus* sp, *Methylobacterium* sp. *Sphingobacterium* sp. *Cellulosimicrobium* sp. *Tepidimonas* sp. *Truepera* sp., *Porphyrobacter* sp., *Novosphingobium* sp., *Exiguobacterium* sp., *Nocardia* sp *Arthrobacter* sp., *Rhodococcus* sp., *Microbacterium* sp., *Kineococcus* sp., and *Williamsia* sp.

The DNA damaging treatment may comprise subjecting the sample to irradiation(s) and/or to one or several genotoxic agents. The treatment is conducted under conditions and/or for a period of time sufficient to induce substantial cell death in the microorganisms present in the sample.

In a preferred embodiment, the DNA damaging treatment comprises subjecting the sample to one or several irradiations. A preferred treatment comprises subjecting the sample (i.e., microorganisms in the sample) to a repeated (e.g., sequential) irradiation treatment.

Irradiation may be selected from UV, gamma and/or X ray irradiation, either alone or in combinations, most preferably UV irradiation(s). Irradiation treatment typically comprises subjecting the microorganisms to one or several sequential irradiations (e.g., from 1 to 5), which may be of the same or different nature, preferably of the same nature. Repeated irradiation treatments are typically carried out at an interval of between 1 and 8 hours, preferably 3 to 5 hours, and more preferably of about 4 hours.

A particularly preferred treatment comprises subjecting the sample to a cell destructing UV irradiation. The invention indeed shows that such a treatment allows to isolate with high efficacy from environmental (e.g., soil or water) samples, under-represented bacteria species producing (secondary) metabolites (such as antibiotics). Cell destructing UV treatments are typically of between 0.5 and 400 mJ/cm2, more preferably of between 1 and 200 mJ/cm2, typically between 1 and 100 mJ/cm2, applied for a period of time of about 5" to 5'. A preferred UV treatment is 4 mJ/cm2 for 30 seconds.

In a specific embodiment, the cell destructing DNA damaging treatment comprises subjecting the sample to at least 2, preferably at least 3 UV treatments of between 0.5 and 400 mJ/cm2 each, preferably of about 4 mJ/cm2 each, carried out at an interval of between 1 and 8 hours, preferably 3 to 5 hours, and more preferably of about 4 hours.

In an alternative method, the cell destructing DNA damaging treatment comprises contacting the sample with a genotoxic agent, such as a solvent, mitomycin, a bleomycin antibiotic, or $H_2O_2$. It should be understood that genotoxic agents may also be used in combination with irradiation. In a particular embodiment, the treatment step b) comprises adding to the sample an effective amount of bleocin, a bleomycin family antibiotic. As illustrated in the examples, the addition of bleocin causes substantial bacterial cell death while allowing rare, metabolite-producing bacteria to grow.

During the treatment phase, the sample is preferably placed in a suitable culture medium such as, without limitation, PGY (Bacto-peptone 10 g/L, Yeast extract 5 g/L, glucose 20 g/L) or LB (Bacto-tryptone 10 g/L, Yeast extract 2.5 g/L, Sodium chloride 10 g/L). It should be understood that other suitable culture media are known to the skilled person (Buchanan et al., 1974, Difco, 1995)) or may be prepared by the skilled person from such known media.

Treatment step b) is typically performed in a solid or semi-solid culture medium, such as in the presence of a gel (e.g., agar). A most preferred treatment medium comprises an agar culture medium, such as a soft agar culture medium. In a particular embodiment, a TGY agar medium is used to grow the bacteria. However, different solid media containing a carbon source, a nitrogen source and mineral salts can be used as well. Serial dilution techniques can also be used according to Schoenborn et al. 2004.

In step c), living or growing bacteria are identified or isolated from the treated sample. Living or growing bacteria may be identified by different means known per se in the art. In a particular embodiment, colonies which form in the culture media are identified. The living or growing bacteria can be isolated and placed in fresh medium for further culture or expansion.

As mentioned above, the method of this invention preferably comprises a step d) of selecting one or several bacteria, from the identified or isolated living or growing bacteria, which produce a particular metabolite. In this regard, it should be noted that steps c) and d) can be performed sequentially, in any order, or simultaneously. For instance, the bacteria in the sample may be placed under conditions suitable to select the desired activity in step b) or c), so that growing or living bacteria identified or isolated in step c) exhibit the desired activity. Alternatively, the bacteria identified or isolated in step c) may be placed under conditions suitable to select the desired activity in step d) only, so that growing or living bacteria are first identified or isolated in step c) and then selected for the desired activity.

The metabolite may be any compound having pharmaceutical and/or agro-chemical interest. In a particular embodiment, the metabolite is a pharmaceutical compound (for use in human or veterinary medicine), preferably selected from antibiotics, bacteriostatic compounds, anti-metabolite, chemotherapeutic compounds, anti-parasitic agents, anti-fungal agents, anti-viral compounds, cytokine-activity compounds or cell-growth factors.

The metabolite may also have utility e.g., in cosmetics or agriculture, such as pigments, insecticides, pesticides, chemical-degrading compounds, etc.

The selection or identification or bacteria producing the selected metabolite can be made according to techniques known per se in the art. In a particular embodiment, step d) comprises exposing identified or isolated bacteria of step c), or an extract thereof, to one or several indicator cells and selecting a bacterium which affect the viability, growth, metabolism, mobility, RNA expression, protein expression, protein secretion or virus production of at least one of said indicator cells.

In the case of antibiotic or antibiostatic agents, the indicator cells are typically reference bacterial strains and test bacteria which inhibit the growth or kill said reference strains are selected.

In the case of, e.g., anti-viral compounds, the indicator cells are typically virus-producing cells and bacteria which affect the production of virus or viability of virus-infected cells are selected.

In this regard, in a particular embodiment, the method of the invention further comprises a step of isolating or purifying the metabolite produced by said bacteria.

In a preferred embodiment, the selected activity is the production of an antibiotic or bacteriostatic activity. The present invention shows that antibiotic-producing bacteria can be isolated with high efficiency from environmental samples treated according to the present method. More particularly, as illustrated in the examples, antibiotic-producing bacteria of the genus *Bacillus, Methylobacterium, Sphingobacterium, Cellulosimicrobium, Tepidimonas, Nocardia, Deinococcus, Truepera, Porphyrobacter* sp., *Novosphingobium* sp., *Exiguobacterium* sp., *Chromobacterium* sp, *Arthrobacter* sp, *Rhodococcus* sp, *Microbacterium* sp, *Kineococcus* sp, or *Williamsia* sp have been isolated from different environmental samples, including water, soil, animal dejection, wood, etc.

The selection of bacteria which produce antibiotics can be performed using different techniques known per se in the art (Singh, 2008, Janssen, 2002, Hamaki, 2005, Schoenborn, L. et al. 2005). In a particular embodiment, the tested bacteria (or an extract thereof) are placed in contact with one or several reference bacterial strains, and the ability of the test bacteria to inhibit the growth of or to kill the reference strains is measured, as an indication of the antibiotic activity. Examples of reference strains include, without limitation, *E. coli, Staphylococcus aureus*, or *Candida tropicalis* (Lorian, 1996).

In this regard, the invention relates to a method to identify or isolate bacteria producing an antibiotic or bacteriostatic agent, the method comprising:

a) providing a sample comprising uncharacterized bacteria;

b) subjecting the sample to a cell destructing DNA damaging treatment, preferably a repeated irradiation treatment, e.g., an UV treatment;

c) identifying or isolating living or growing bacteria from said treated sample; and d) exposing identified or isolated bacteria of step c), or an extract thereof, to a reference bacterial strain and identifying or isolating bacteria which exhibit an antibiotic or bacteriostatic activity.

The method may further comprise a step of isolating or purifying the antibiotic produced by said bacteria.

A further object of this invention is a method to identify or isolate anti-metabolite or chemotherapeutic or anti-fungal or cytokine activity or cell-growth factor producing bacteria, the method comprising:

a) providing a sample comprising uncharacterized bacteria;

b) subjecting the sample to a cell destructing DNA damaging treatment, preferably a repeated irradiation treatment, e.g., an UV treatment;

c) identifying or isolating living or growing bacteria from said treated sample; and d) exposing identified or isolated bacteria of step c), or an extract thereof, to one or several reference eukaryotic cell types and identifying selected bacteria which affect the viability, growth, metabolism, mobility, RNA expression, protein expression, or protein secretion of some of the eukaryotic cell types.

The method may further comprise a step of isolating or purifying the anti-metabolite or chemotherapeutic or anti-fungal or cytokine activity or cell-growth factor produced by said bacteria.

A further object of the invention resides in a method to identify or isolate anti-viral compound producing bacteria, the method comprising:

a) providing a sample comprising uncharacterized bacteria;

b) subjecting the sample to a cell destructing DNA damaging treatment, preferably a repeated irradiation treatment, e.g., an UV treatment;

c) identifying or isolating living or growing bacteria from said treated sample; and d) exposing identified or isolated bacteria of step c), or an extract thereof, to one or several virus-producing cell types to select bacteria which affect the production of virus or viability of virus-infected cells.

The method may further comprise a step of isolating or purifying the anti-viral agent produced by said bacteria.

The methods of the present invention may also include a step of determining the genus/species of the identified or isolated bacteria. In this respect, the invention is particularly suited for identifying or isolating *Deinococcus* bacteria which produce a selected metabolite.

Accordingly, in a particular embodiment, the invention relates to a method for identifying or isolating a bacterium which exhibit a selected activity (e.g. which produces a metabolite of interest), the method comprising:

a) providing a sample comprising uncharacterized bacteria;

b) subjecting the sample to a cell destructing DNA damaging treatment, preferably a repeated irradiation treatment;

c) identifying or isolating living or growing *Deinococcus* bacteria from said treated sample; and d) selecting *Deinococcus* bacteria of step c) which exhibit the selected activity.

The bacteria can be characterized and classified e.g., according to Hirsch, 2004 and Kampfer, 2008. The physiological characterization includes for instance the determination of the fatty acid, respiratory quinones, polar lipids and polyamines patterns, a metabolic profiling of different sources of carbon and/or the determination of the 16S rDNA gene sequences.

Furthermore, the methods of this invention can comprise one or several additional steps of selecting bacteria having particular properties. More particularly, in a preferred embodiment, the method further comprises one or several steps of selecting bacteria which are viable or grow under selected culture conditions, such as media, temperature, pH, salinity, nutrients, oxygenation or carbon source. For this purpose, the sample or bacteria can be placed under appropriate selection conditions during any one of steps b), c) or d), or during a prior or subsequent step, and the resulting property is selected for during any of these steps.

In a particular aspect of the present invention, the bacteria are cultured under particular temperature conditions in order to identify or isolate bacteria which are viable or can be grown in a temperature range from approximately 4 to 70° C. More particularly, the bacteria are maintained at the selected temperature during step b), c) and/or d); and/or during an additional step e), in order to identify or isolate bacteria which are viable or can be grown at the desired temperature.

In another particular aspect of the present invention, the bacteria are cultured under particular saline conditions in order to identify or isolate bacteria which are viable or can be grown under concentration conditions of NaCl or equivalent salts possibly reaching around 5% weight/volume. More particularly, the bacteria are maintained at the selected salinity during step b), c) and/or d), and/or during an additional step e), in order to identify or isolate bacteria which are viable or can be grown at the desired salinity.

In a further particular and preferred embodiment of the present invention, the bacteria are cultured under particular pH conditions in order to identify or isolate bacteria which are viable or can be grown in a pH interval between approximately 3 and 9.5, preferably between 4 and 8. More particularly, the bacteria are maintained at the selected pH during step b), c) and/or d); and/or during an additional step e), in order to identify or isolate bacteria which are viable or can be grown at the desired pH.

In a further particular embodiment of the present invention, the bacteria are cultured under particular oxygenation conditions in order to identify or isolate bacteria which are viable or can be grown in aerobic and/or anaerobic conditions. More particularly, the bacteria are maintained under the selected oxygenation conditions during step b), c) and/or d); and/or during an additional step e), in order to identify or isolate bacteria which are viable or can be grown at the desired conditions.

In a further particular embodiment of the present invention, the bacteria are cultured in a particular culture medium in order to identify or isolate bacteria which are viable or can be grown in the presence of a selected carbon source. More particularly, the bacteria are maintained under the medium during step b), c) and/or d); and/or during an additional step e), in order to identify or isolate bacteria which are viable or can be grown using the desired carbon source.

It should be understood that the above characteristics can be selected individually or in any combinations. For instance, the method can be used to identify bacteria which are viable or can be grown at a desired temperature and salinity, or at a desired temperature and pH, or at a desired temperature, pH and oxygenation condition. Furthermore, the methods of this invention may comprise a further step of modifying, e.g., either biologically, genetically and/or chemically, the identified or isolated bacteria, or their DNA, by any process known per se in the art, said modification aiming e.g., to improve the viability, growth or functions of the said bacterium, e.g., in order to improve the antibiotic activity. Such modification step includes, without limitation, cell fusion, accelerated evolution, DNA shuffling, mutagenesis, insertion of eukaryote, prokaryote or synthetic nucleic acid (e.g., DNA) from another strain, or any genetic engineering technology. The modification may also include a step of introducing a marker gene (e.g., kanamycin resistance) in the bacterium.

Many (marketed) antibacterial drugs are semisynthetic analogs of natural products, and are obtained from modifications of initial fermentation products. This is the case for Ketolides, the β-lactam group of antibiotics. Semisynthesis or even manipulation of the enzymes involved in the antibiotic biosynthesis can therefore be used to improve the initial hit (Von Nussbaum, 2006, Marsden, 1998).

Accordingly, in a particular embodiment, the invention resides in a method of producing a bacterium having a selected activity, the method comprising isolating a bacterium according to any of the above described methods and modifying said bacterium e.g., by genetic, biologic or chemical treatment to improve said activity.

As illustrated in the examples, the method of the present invention has allowed the efficient and rapid isolation of UV-resistant bacteria which produce secondary metabolites (e.g., antibiotics). These bacteria were unknown before and can extend the diversity and spectrum of antibiotic activity (or other secondary metabolites) for therapeutic or other industrial purposes.

A further aspect of this invention therefore also resides in a bacterium obtainable by a method as disclosed above, or an extract thereof. The extract may be any preparation derived from a cell culture, such as a supernatant, a lysate, a cell membrane, or enriched/purified preparations derived therefrom, preferably containing a secondary metabolite.

The bacterium may belong to different genus, such as, e.g., *Bacillus, Methylobacterium, Sphingobacterium, Cellulosimicrobium, Tepidimonas, Nocardia, Deinococcus, Truepera, Porphyrobacter* sp., *Novosphingobium* sp., *Exiguobacterium* sp., *Chromobacterium* sp, *Arthrobacter* sp, *Rhodococcus* sp, *Microbacterium* sp, *Kineococcus* sp, or *Williamsia* sp.

The invention also relates to a method of producing a recombinant host cell, the method comprising identifying or isolating or producing a bacterium according to any one of the methods as defined above and cloning genes (or gene clusters or operons, or corresponding synthetic or recombinant nucleic acids) from said bacterium into another host cell, thereby producing a recombinant host cell. The host cell may be a prokaryotic or eukaryotic host cell, preferably a prokaryotic host cell. Cloning can be made according to techniques known per se in the art, such as using cloning vectors (e.g., plasmids, phages, bacterial chromosomes, etc.). In a preferred embodiment, genes or gene clusters encoding all or part of a biosynthetic pathway (e.g., genes encoding enzymes involved in such pathways) are isolated from the identified bacterium, cloned into appropriate vectors, and inserted into the selected host cell, to build new biosynthetic pathways.

Drug Microbial Production

The invention also relates to a method of producing a pharmaceutical agent (such as an antibiotic), the method comprising identifying or isolating or producing bacterium according to any one of the above methods, wherein said bacterium produces the pharmaceutical agent, and producing said antibiotic. Production of the pharmaceutical agent may comprise culturing the bacterium (or progeny or derivatives thereof) under suitable conditions are collecting or purifying the agent. Production of the agent may also comprise artificial synthesis (e.g., chemical, recombinant, enzymatic, etc.).

A further object of this invention is a method of identifying, isolating or producing a pharmaceutical agent (such as an antibiotic), using a wild type *Deinococcus* bacterial strain or a related bacterium.

A further object of this invention is a method of identifying, isolating or producing a pharmaceutical agent (such as an antibiotic), using a modified *Deinococcus* bacterial strain.

A further object of this invention resides in the use of a *Deinococcus* or related bacterium to produce a pharmaceutical agent (such as an antibiotic).

Within the context of the present invention, the terms "pharmaceutical agent" and "drug" are used interchangeably and designate any substance (suitable for use in a pharmaceutical or veterinary product) which exhibits a pharmacological activity and/or which have a direct effect in the cure, mitigation, treatment or prevention of a disease, and/or which have direct effect in restoring, correcting or modifying a physiological function in a human being or in a non-human animal.

The term "drug" includes, for instance, any chemical substance used in the treatment, cure, prevention, or diagnosis of a disease or used to otherwise enhance physical or mental well-being in mammals, particularly in human beings.

Specific examples of drugs include, without limitation, antibiotics, bacteriostatic compounds, anti-metabolite, chemotherapeutic compounds, antioxidants, anti-inflammatory, polysaccharides, anti-parasitic agents, anti-fungal agents, anti-viral compounds, cytokine-activity compounds, cell-growth factors, hormones, anti-depressives, anti-migraine, anti-asthma, contraceptives, anti-diabetics, psychotropic, anti anti-arrhythmics, enzyme-inhibitors, or adjuvants.

The term "drug" also includes, generally, any agent that improves or modifies Health or well-being, alicaments, probiotics, etc.

Probiotics designate live microorganisms that, when administered in adequate amounts, confer a health benefit on the host (Sanders M E. 2008 Probiotics: definition, sources, selection, and uses. *Clin Infect Dis*. February 1; 46). Probiotics may facilitate a return to normal status after a perturbation of the microbiota (e.g., because of the use of antibiotics or illness), they may aid in establishing the best balance of microorganisms or to improve the balance of the intestinal microbiota, (Balcazar et al., 2006. The role of probiotics in aquaculture. *Veterinary Microbiology* 114, 173-186). Others benefits of probiotics include (i) competitive exclusion of pathogenic bacteria, (ii) source of nutrients and enzymatic contribution to digestion; (iii) direct uptake of dissolved organic material mediated by the bacteria or (iv) enhancement of the immune response against pathogenic microorganisms.

For use as probiotics for human food, *Deinococcus* sp. may be formulated in e.g., yogurt or fermented milk or drinks, typically at a dosage of between about $1 \cdot 10^6$ and about $1 \cdot 10^9$ CFU per day or per dose.

The pharmaceutical agent or drug may be a small chemical compound, a peptide, a protein, a lipid, a polysaccharide, a nucleic acid, etc.

In this regard, a particular object of the invention lies in a method for producing a drug, comprising (i) culturing, in a suitable medium, a bacterium which produces said drug or an intermediate (or precursor) thereof, (ii) collecting or purifying the drug or intermediate from the culture, and (iii) when an intermediate is produced in step (i), converting said intermediate into said drug, wherein said bacterium is a *Deinococcus* or a related bacterium.

Within the context of the present invention, an "intermediate" of a drug refers to any substance formed in the course of the reactions that lead to said drug. Such intermediate may exhibit a pharmacological activity. According to the invention, the term "intermediate" encompasses the prodrugs. For instance, a prodrug may designate an inactive intermediate whose metabolism may lead to an active metabolite, i.e. the drug.

Another particular object of the invention is an improved method for the production of a drug from a cultured microbial cell, the improvement consisting in the use, as said microbial cell, of a *Deinococcus* or related bacterium.

A further object of the invention relates to a method for producing a drug by transformation of a precursor thereof, said method comprising exposing the precursor to a catalyst and collecting the drug resulting from the transformation, wherein the catalyst is a *Deinococcus* or a related bacterium, or an extract thereof.

Upon production, or isolation or collection, the drug may be used as such or may be further chemically modified, as appropriate. Also, the drug may be formulated in any appropriate composition using suitable excipients, diluents or carriers.

A further object of this invention is an antibiotic derived from a *Deinococcus* bacterium.

A further object of this invention is an antioxidant derived from a *Deinococcus* bacterium.

A further object of the invention is a pharmaceutical composition comprising a *Deinococcus* bacterium.

A further object of the invention is a food additive composition comprising a *Deinococcus* bacterium.

A further object of the invention is a composition comprising a *Deinococcus* bacterium as an intestinal flora modifier.

The invention discloses the ability of *Deinococcus* bacteria to naturally produce drugs of high value or interest, or precursors thereof. The invention may therefore use such bacteria without further modification, or use improved or modified bacteria with increased production levels or quality. In particular, the bacteria may be selected by culture in appropriate conditions and medium to selected best clones, or cultured under selection/evolution pressure to increase the performance, and/or genetically modified.

Specific examples of *Deinococcus*-related bacteria include *Microbacterium* sp, *Promicromonospora* sp, and *Chromobacterium haemolyticum*.

Also, the present invention can be used to select bacteria and to generate metagenomic libraries. Typically genomic DNA from such bacteria is extracted and large fragments of DNA are (directly) cloned in a shuttle vector to make a metagenomic library representative of said bacteria. This metagenomic library can be transferred into different host bacteria to identify secondary metabolite producing strains. As an example, enzymes responsible for polyketide production can be screened according to Ginolhac, 2007.

Furthermore, the invention also relates to improved industrial methods of using microorganisms. Indeed, the invention also proposes to include one or several cell destructing DNA damaging treatments into industrial processes in order to eliminate potentially contaminating bacteria. Indeed, since bacteria of the present invention are able to grow and survive such cell-destructing treatments, the latter may be used, e.g., in any industrial fermentation or culture device or installation, to avoid contamination. In this respect, a particular object of this invention also resides in a process of using a bacterium obtainable by a method as described above in a fermentation or continuous culture, wherein the process comprises a step of irradiation of the bacterium prior to or following initiation of the fermentation or of the continuous culture, to limit contamination by other bacteria or cells. A further object of this invention is a process of using a *Deinococcus* bacterium in a fermentation or continuous culture, wherein the process comprises a step of irradiation of the bacterium prior to or following initiation of the fermentation or of the continuous culture, to limit contamination by other bacteria or cells. Irradiation may be performed repeatedly, typically under the conditions described above.

Further aspects and advantages of the instant invention will be disclosed in the following examples, which should be regarded as illustrative and not limiting. All references (patent applications, patents, scientific publications) cited in this application are incorporated therein by reference.

EXAMPLES

Example 1

Determination of Improved Conditions for Selecting Metabolite-Producing Bacterium In a preliminary step, 5 strains were tested for their resistance to UV. These strains were *E. coli, Deinococcus radiopugnans, Deinococcus radiodurans, Deinococcus* sp. and *Deinococcus geothermalis.*

Stationary phase cultures of the 5 tested strains were successively diluted from $10^0$ to $10^{-8}$. All dilution were spotted (5 μL) on agar rich media TGY (Trypton 10 g/l, Glucose 2.5 g/L and Yeast extract 5 g/L) and different UV-treatments were applied: 0 mJ/cm$^2$, 4 mJ/cm$^2$, 17 mJ/cm$^2$, 42 mJ/cm$^2$ and 167 mJ/cm$^2$ with a BioLink crosslinker (Vilbert Lourmat).

Table 1 below presents the bacterial density after different UV treatments.

TABLE 1

| Strains | 0 mJ/cm$^2$ | 4 mJ/cm$^2$ | 17 mJ/cm$^2$ | 42 mJ/cm$^2$ | 167 mJ/cm$^2$ |
|---|---|---|---|---|---|
| *D. radiopugnans* (CFU/ml) | 4.00E+09 | 1.00E+09 | 1.60E+08 | 6.00E+05 | 0.00E+00 |
| *D. radiodurans* (CFU/ml) | 2.00E+07 | 6.00E+06 | 2.00E+06 | 2.00E+03 | 0.00E+00 |
| *E. coli* (CFU/ml) | 3.00E+07 | 2.00E+04 | 0.00E+00 | 0.00E+00 | 0.00E+00 |
| *D. geothermalis* (CFU/ml) | 1.20E+09 | 6.00E+08 | 8.00E+05 | 0.00E+00 | 0.00E+00 |
| *Deinococcus* sp. (CFU/ml) | 8.00E+08 | 2.20E+08 | 6.00E+06 | 4.00E+03 | 0.00E+00 |

As can be seen, a treatment of 4 mJ/cm$^2$ reduces by 3 log the bacterial titer in a culture of *E. coli*. A treatment of 17 mJ/cm$^2$ also discriminates between *E coli* and *Deinococcus* bacteria.

In a second step, a soil suspension was subjected to different irradiation treatments based on the results of table 1. The soil suspension was prepared as follows: 5 g of wet soil was diluted in 20 mL distilled water. After vortex and sonication (1 minute), soil supernatant was collected and mixed with a 350 μL *D. radiopugnans* culture in stationary growth phase. An aliquot (50 μL) was spread on TGY agar containing an antifungal (cycloheximide, 100 μg/mL), and different repeated sequential irradiation treatments were tested: 1 treatment, 2 treatments and 3 treatments. 4 h-intervals was respected between each UV treatment.

Figure 1B:
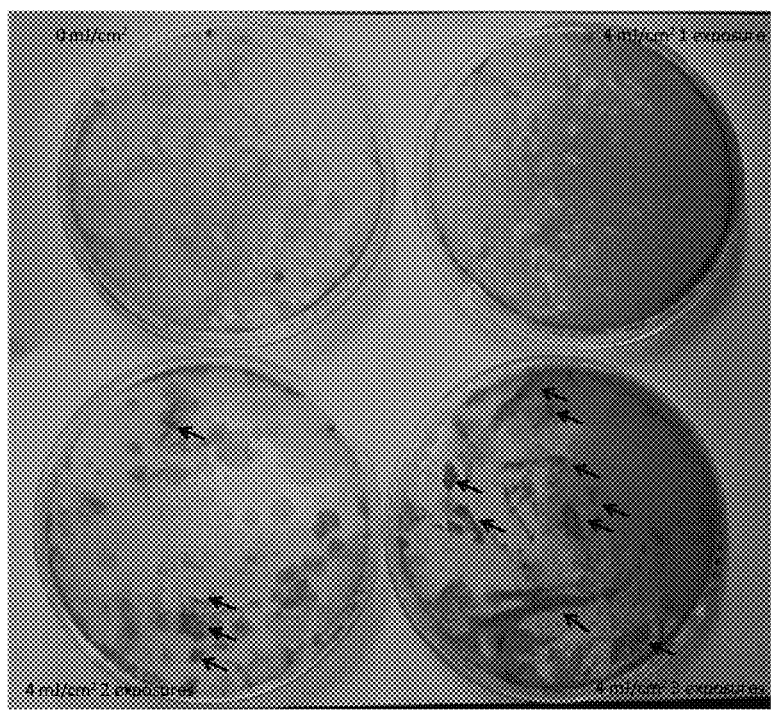

FIG. 1a shows the results obtained after one exposure at 0 mJ/cm$^2$, 4 mJ/cm$^2$ and 17 mJ/cm$^2$. FIG. 1b shows the results obtained after 1, 2 and 3 exposures to 4 mJ/cm$^2$.

As can be seen, the best tested conditions are 3 exposures to UV irradiations of 4 mJ/cm$^2$ each. Such conditions provide the highest amount of growing *Deinococcus* bacteria from the treated soil sample. A substantial amount of *Deinococcus* bacteria is also obtained after one exposure of the sample to UV irradiation of 17 mJ/cm$^2$.

Example 2

Isolation of UV-Resistant Bacteria from Water Samples

Water samples were concentrated by filtration over a 0.22 μm nitrocellulose filter (Millipore, France), then placed in suspension in 10 ml of sterile water. The filtered solution is then sonicated for approximately 60 seconds to resuspend the bacteria.

Following sonication, between 150 μl and 2 ml of the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l, and yeast extract (Fluka, France) 5 g/l. The seeded culture then undergo 3 UV treatments of 4 mJ/cm$^2$ each using a BLX-E254 biolink (Vilber-Lourmat, France), carried out at an interval of 4 hours. After incubation at 30 to 50° C. for 3 to 4 days, the viable colonies of interest were visible.

Examples of colonies identified are listed in Table 2 below.

Example 3

Isolation of UV-Resistant Bacteria from Wood and Pebble Samples

Wood and pebble samples were immersed in sterile water then vortexed and sonicated for approximately 60 seconds.

Following sonication, between 150 μl and 2 ml of the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l, and yeast extract (Fluka, France) 5 g/l. The seeded culture media then undergo 3 UV treatments using a BLX-E254 biolink (Vilber-Lourmat, France) of 4 mJ/cm2 each, carried out at an interval of 4 hours. After incubation at 30 to 50° C. for 3 to 4 days, the viable colonies of interest were visible.

Examples of colonies identified are listed in Table 2 below.

Example 4

Isolation of UV-Resistant Bacteria from Stones, Moss, Lichen, Mud, Sediment, Biofilm, Soil and Animal Dejection Samples of moss, lichen, mud, soil and animal dejection were placed in suspension in sterile water (V/V) then vortexed. The samples were then sonicated for approximately 60 seconds.

Following sonication, between 150 μl and 2 ml of the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l, and yeast extract (Fluka, France) 5 g/l. The seeded culture media then undergo 3 UV treatments using a BLX-E254 biolink (Vilber-Lourmat, France) of 4 mJ/cm2 each, carried out at an interval of 4 hours. After incubation at 30 to 50° C. for 3 to 4 days, the viable colonies of interest are visible.

Examples of colonies identified are listed in Table 2.

TABLE 2

| Biotope | Genus | Isolation t ° C. |
| --- | --- | --- |
| Pebble | Bacillus | 30° C. |
| Stones | Methylobacterium | 30° C. |
| Animal dejection | Sphingobacterium | 30° C. |
| Stones | Cellulosimicrobium | 30° C. |
| Water | Tepidimonas | 45° C. |
| Water | Deinococcus | 45° C. |
| Pebble | Deinococcus | 30° C. |
| Muck, pebble, soil | Chromobacterium | 30° C. |

Example 5

Isolation of Bacteria from Bleocin-Treated Samples

Soil samples containing *Deinococcus radiopugnans* strain DRH$_{40}$ were placed in suspension under conditions similar to that of example 2. In place of irradiation, the suspensions were maintained in the absence (control) or presence of 50 μg/ml or 100 μg/ml of bleocin.

In the absence of bleocin, no growing pink colonies (*Deinococcus*) are observed, but only indigenous microflora. In the presence of 50 μg/ml bleocin, indigenous microflora decreases drastically, and pink colonies are present. The same phenomenon is observed at 100 μg/ml of bleocin.

Example 6

Identification of Antibiotic Producing Bacteria

The UV resistant strains as disclosed in Table 2 were tested for their ability to inhibit the growth of several reference strains of bacteria. Briefly, fermentation was carried out in 10 ml PGY medium containing peptone 5 g/L, yeast extract 2.5 g/L and glucose 0.5 g/L at 30 to 50° C. with aeration and agitation. After 3 days the antibiotic production of the tested strains was controlled and quantified by diffusion test agar against several reference strains cultivated on LB medium.

LB: Bacto-tryptone 10 g/L, Yeast extract 5 g/L, Sodium chloride 10 g/L.

PGY: peptone 5 g/L, yeast extract 2.5 g/L, glucose 0.5 g/L.
Reference Strains:
*Staphylococcus aureus* CIP 76.25;
*Escherichia coli* CIP 76.24;
*Candida tropicalis* CIP 1275.

The results are depicted in Table 3 below.

TABLE 3

| Tested Bacteria | *Staphylococcus aureus* CIP 76.25 | *Escherichia coli* CIP 76.24 | *Candida tropicalis* CIP 1275 |
| --- | --- | --- | --- |
| Strain 1 | 0 | + | + |
| Strain 2 | + | + | 0 |
| Strain 3 | 0 | 0 | 0 |
| Strain 4 | + | 0 | 0 |
| Strain 5 | + | 0 | 0 |
| Strain 6 | 0 | 0 | + |
| Deinococcus | 0 | + | 0 |

0: no visible antibiosis;
+: visible antibiosis

The results show that several strains exhibiting antibiotic activity have been isolated. These strains produce antibiotic activity which is active against *Staphylococcus aureus*, *Escherichia coli* and/or *Candida tropicalis*. The producing strains are resistant to UV and can be grown at elevated temperature, thereby illustrating the efficacy of the method of this invention.

Example 7

Antibiotic Production Screening Assay 7.1. Material and Method
Culture Media

Different media were prepared to test antibiotic production.

100 mL of solution A is composed by MnCl$_2$, 4H$_2$O 0.1 g, ZnSO$_4$, 7H$_2$O 0.1 g and FeCl$_3$ 0.1 g.

Medium 1 is composed by bacto peptone from casein 5 g/L, bacto yeast extract 3 g/L and adjusted at pH 7.1.

Medium 2 is composed by cellobiose 10 g/L, K$_2$HPO$_4$ 1 g/L, MgSO$_4$, 7H$_2$O 1 g/L, NaCl1 g/L, (NH$_4$)$_2$SO$_4$ 2 g/L, CaCO$_3$ 2 g/L and adjusted at pH 7.2. Solution A is added at 1 ml/L.

Medium 3 is composed by oatmeal 20 g/L and solution A at 1 ml/L.
Culture Preparation of Test Strains Strains were inoculated in 5 mL of PGY liquid media. Precultures were then incubated at 30° C. or 45° C. for 48 hours under shaking at 150 rpm.

In 15 mL-glass tube, 100 μL of preculture were inoculated in 5 mL of media 1 to 3. Cultures were then incubated at 30° C. or 45° C. for 48 hours, 96 hours, 168 hours and 336 hours under shaking at 150 rpm.
Culture Preparation of Target Strains Target strains were *Staphylococcus aureus* CIP76.25, *Escherichia coli* CIP 76.24, *Pseudomonas aeruginosa* CIP 76.110, *Streptococcus pneumonia* CIP 104485 and *Candida tropicalis* DSM 1346.

They were cultivated on LB medium at 37° C. for 18 hours. Then, 10 mL soft agar (Luria Bertani medium with agar at 7 g/L) were inoculated at 2% (v/v) with preculture of target strains in a petri dish.
Evaluation of Antibiotic Production After incubation at 30° C. or 45° C. for 48 hours, 96 hours, 168 hours and 336 hours, 1 mL-test culture was centrifuged at 13000 rpm for 3 minutes. The supernatant was then filtered on 0.22 μm-filter. 10 μL of filtered culture supernatant was inoculated on soft agar containing target strains. After incubation at 37° C. for 18 hours, lysis plaques could be observed.
7.2. Results Table 4 presents example of different obtained antibiotic profiles. *Kineococcus* strain M10-5H produced antibiotics against Gram positive test strains and *E. coli* CIP 76.24. *Deinococcus* strain MC$_{5-7}$F produced antibiotics against *S. aureus* CIP 76.25. *Microbacterium* strain MA3-7G produced antibiotics against *C. tropicalis* CIP 1275 and *Williamsia* strain MA3-6B produced antibiotics against Gram positive test strains and *P. aeruginosa* CIP 76.110.

TABLE 4

Results of antibiotic production tests

| | Staphylococcus aureus CIP 76.25 | Streptococcus pneumonia CIP 104485 | Pseudomonas aeruginosa CIP 76.110 | Escherichia coli CIP 76.24 | Candida tropicalis CIP 1275 |
|---|---|---|---|---|---|
| Kineococcus M10-5H | + | + | − | + | + |
| Deinococcus MC5-7F | + | − | − | − | − |
| Microbacterium MA3-7G | − | − | − | − | + |
| Williamsia MA3-6B | + | + | + | − | − |

"+" means that an antibiosis has been observed.
"−" means that no antibiosis has been observed.

Example 8

Production of Antioxidants by *Deinococcus*

The present example discloses the production of antioxidants from *Deinococcus*. The example shows *Deinococcus* bacteria produce substantial amounts of carotenoids, which can be isolated and used as an antioxidant. Alternatively, the whole bacteria, or extracts thereof, can be used as antioxidant agent.

8.1. Materials & Methods

Cultures of the *Deinococcus* strains were performed at 30° C., 150 rpm, in CMG medium containing glucose 1%. After, 48 hours, the culture is centrifuged to obtain a pellet, the supernatant being discarded. The extraction of carotenoids is performed with 3 washes of 1 ml methanol. Then, the quantity of carotenoids in the extraction fractions is determined after reading OD at 480 nm with the following extinction coefficient of carotenoids (137000 $M^{-1} \cdot cm^{-1}$).

8.2. Results

The results are presented in the table below:

| Strains | mg carotenoids/ g dry weight |
|---|---|
| *Deinococcus radiopugnans* DSM 12027 DRH11 | 1.72 |
| *Deinococcus* M3-2D | 1.01 |
| *Deinococcus* M1-8D | 0.47 |
| *Deinococcus* M2-8C | 0.44 |

These results show that *Deinococcus* strains produce naturally high amounts of carotenoids that are known to act as anti-oxidant.

Example 9

Production of Cytotoxic Agents by *Deinococcus* or Related Bacteria

The present example discloses the production of cytotoxic agents from *Deinococcus*. The example shows *Deinococcus* bacteria produce substantial amounts of cytotoxic agents, which can be isolated and used as active pharmaceutical ingredients.

9.1. Material & Methods:

*Deinococcus* strains M36-7D, MA3-11A, M45-6E and MA12-4C were grown in PGY medium until stationary phase. Different samples have been taken throughout the growth and diluted at different concentrations (dilution factors: 1/4, 1/8, 1/16, 1/32, 1/64) and then tested for their toxicity against cancerous human cell lines HT29 and MRC5 by using the in vitro toxicology assay kit, MTT based from Sigma-Aldrich. The experiments have been performed according to the Sigma Aldrich toxicology assay protocol.

9.2. Results

The results are presented in the following table.

TABLE

Percentage of inhibition of eukaryotic cells growth

| | | | HT29 cells | | | | | MRC5 cells | | | |
|---|---|---|---|---|---|---|---|---|---|---|---|
| | | N° | Dilution factor | | | | | | | | |
| Strains | | fraction | 1/4 | 1/8 | 1/16 | 1/32 | 1/64 | 1/4 | 1/8 | 1/16 | 1/32 | 1/64 |
| *Deinococcus geothermalis* | M36-7D | 9 | 100 | nd | nd | 0 | 1 | nd | 6 | 0 | 0 | 0 |
| | M36-7D | 5 | nd | nd | 100 | 35 | 15 | 0 | 0 | 0 | 0 | 0 |
| | M36-7D | 2 | 52 | 0 | 88 | 31 | 57 | 100 | 100 | 70 | 36 | 35 |
| *Microbacterium* sp. | MA3-11A | 2 | 11 | 69 | 74 | nd | nd | 83 | 99 | 38 | nd | nd |
| | MA3-11A | 12 | 19 | 58 | 32 | nd | nd | 100 | 0 | 0 | nd | nd |
| *Promicromonospora* | M45-6E | 2 | 97 | 94 | 88 | 46 | 53 | 93 | 96 | 94 | 11 | 0 |
| | M45-6E | 3 | 91 | 93 | 87 | 66 | 59 | 79 | 88 | 60 | 25 | 2 |
| | M45-6E | 14 | nd | nd | nd | 4 | 6 | 100 | 0 | 0 | 0 | 0 |

TABLE-continued

Percentage of inhibition of eukaryotic cells growth

| Strains | N° | N° fraction | HT29 cells | | | | | MRC5 cells | | | | |
| --- | --- | --- | --- | --- | --- | --- | --- | --- | --- | --- | --- | --- |
| | | | Dilution factor | | | | | | | | | |
| | | | 1/4 | 1/8 | 1/16 | 1/32 | 1/64 | 1/4 | 1/8 | 1/16 | 1/32 | 1/64 |
| *Chromobacterium haemolyticum* | MA12-4C | 3 | 91 | 74 | 79 | 83 | 89 | 0 | 10 | 24 | 27 | 24 |
| | MA12-4C | 9 | 71 | 89 | 92 | 96 | 94 | 1 | 3 | 85 | 79 | 80 |
| | MA12-4C | 19 | 94 | 88 | 95 | 92 | 89 | 85 | 92 | 81 | 79 | 84 |
| | MA12-4C | 22 | 87 | 94 | 92 | 97 | 86 | 96 | 95 | 94 | 94 | 94 |

These results show that all strains have an inhibitory effect on the growth of eukaryotic cells HT29 and/or MRC5. Several culture fractions of *Deinococcus* strains M36-7D (fractions n° 9, 5 and 2) abolished totally the growth of both HT29 and MRC5 eukaryotic cells when diluted up to 16-fold. In addition, Fractions n° 2 and 12 induce 100% of growth inhibition of MRC5 cells when diluted to 4- and 8-fold, respectively. Interestingly, culture fraction n° 9 of MA12-4C strain showed very good toxicity effect on HT29 cells even at high dilution rate. These results therefore demonstrate that *Deinococcus* produce efficient cytotoxic agents, which can be isolated and used as active pharmaceutical ingredients.

Example 10

*Deinococcus* Cultivation in Bioreactor for Industrial Drug Production

*Deinococcus geothermalis* is cultivated on R2YE medium without Phosphate addition in 1 L-bioreactor (Biostat Q+Sartorius). The temperature and pH is maintained at 45° C., and 6 respectively. The aeration is kept at 0.1 vvm and pO2 at 20% with a cascade regulation on stirrer between 400 and 1000 rpm. The following composition of culture medium R2YE: $K_2SO_4$ 1.23 mM; $MgCl_2.6H_2O$ 50 mM; Glucose 55.5 mM (10 g/L); $CaCl_2.2H_2O$ 20 mM; $ZnCl_2$ 0.08 mg/L; $FeCl_3.6H_2O$ 0.4 mg/L; $CuCl_2.2H_2O$ 0.02 mg/L; $MnCl_2.4H_2O$ 0.02 mg/L; $Na_2B_4O_7.10H_2O$ 0.02 mg/L; $(NH_4)_6Mo_7O_{24}.4H_2O$ 0.02 mg/L, Yeast Extract 5 g/L. The drug can be isolated or purified using conventional techniques.

REFERENCES

Bérdy J Bioactive microbial metabolites. J Antibiot (Tokyo). 2005 January; 58(1):1-26, Erratum in: J Antibiot (Tokyo). 2005 April; 58(4):C-1.

Buchanan R and Gibbons N Bergey's manual of determinative bacteriology (1974) 8th ed., DIFCO manual Dehydrated Culture Media and Reagents for Microbiology (1995) Eds DIFCO, 11th ed.

Ginolhac A, Jarrin C, Gillet B, Robe P, Pujic P, Tuphile K, Bertrand H, Vogel T M, Perrière G, Simonet P, Nalin R Phylogenetic analysis of polyketide synthase I domains from soil metagenomic libraries allows selection of promising clones. Appl Environ Microbiol. 2004 September; 70(9):5522-7.

Hamaki T, Suzuki M, Fudou R, Jojima Y, Kajiura T, Tabuchi A, Sen K, Shibai H Isolation of novel bacteria and actinomycetes using soil-extract agar medium. J Biosci Bioeng. 2005 May; 99(5):485-92.

Hirsch P, Gallikowski C A, Siebert J, Peissl K, Kroppenstedt R, Schumann P, Stackebrandt E, Anderson R *Deinococcus frigens* sp. nov., *Deinococcus saxicola* sp. nov., and *Deinococcus marmoris* sp. nov., low temperature and draught-tolerating, UV-resistant bacteria from continental Antarctica. Syst Appl Microbiol. 2004 November; 27(6):636-45.

Janssen P, Yates P, Grinton B, Taylor P, and Sait M Improved Culturability of Soil Bacteria and Isolation in Pure Culture of Novel Members of the Divisions *Acidobacteria, Actinobacteria, Proteobacteria,* and *Verrucomicrobia* Applied and Environmental Microbiology, May 2002, p. 2391-2396, Vol. 68, No. 5.

Kämpfer P, Lodders N, Huber B, Falsen E, Busse H J *Deinococcus aquatilis* sp. nov., isolated from water. Int J Syst Evol Microbiol. 2008 December; 58(Pt 12):2803-6.

Lorian V (ed.), Antibiotics in laboratory medicine. Williams & Wilkins, Baltimore, Md. 1996.

Makarova K S, Aravind L, Wolf Y I, Tatusov R L, Minton K W, Koonin E V, Daly M J Genome of the extremely radiation-resistant bacterium *Deinococcus radiodurans* viewed from the perspective of comparative genomics Microbiol Mol Biol Rev. 2001 March; 65(1):44-79.

Marsden A F, Wilkinson B, Cortes J, Dunster N J, Staunton J, Leadlay P F Engineering broader specificity into an antibiotic-producing polyketide synthase. Science. 1998 Jan. 9; 279(5348):199-202.

Rainey F, Ray K, Ferreira M, Gatz B, Nobre M, Bagaley D, Rash B, Park M, Earl A, Shank N, Small A, Renk M, Battista J, Kämpfer P, and da Costa M Extensive Diversity of Ionizing-Radiation-Resistant Bacteria Recovered from Sonoran Desert Soil and Description of Nine New Species of the Genus *Deinococcus* Obtained from a Single Soil Sample Appl Environ Microbiol. 2005 September; 71(9): 5225-5235.

Reichenbach H Myxobacteria, producers of novel bioactive substances. J Ind Microbiol Biotechnol. 2001 September; 27(3):149-56.

Schoenborn L, Yates P, Grinton B, Hugenholtz P, and Janssen P Liquid Serial Dilution Is Inferior to Solid Media for Isolation of Cultures Representative of the Phylum-Level Diversity of Soil Bacteria Applied and Environmental Microbiology, July 2004, p. 4363-4366, Vol. 70, No. 7.

Singh S B, Pelaez F Biodiversity, chemical diversity and drug discovery. Prog Drug Res. 2008; 65:141, 143-74.

von Nussbaum F, Brands M, Hinzen B, Weigand S, Häbich D Antibacterial natural products in medicinal chemistry—exodus or revival? Angew Chem Int Ed Engl. 2006 Aug. 4; 45(31):5072-129.

Yang B, Xue Q H, Chen Z Q, Zhou Y Q, Zhang X L, Xu Y J, Guo Z Y Effects of microwave irradiation on isolation of soil actinomycetes, Ying Yong Sheng Tai Xue Bao. 2008 May; 19(5):1091-8.

We claim:

1. A method for producing an antibiotic, the method comprising (i) culturing, in a suitable medium, a *Deinococcus* bacterium which naturally produces said antibiotic or an intermediate thereof, (ii) collecting or purifying the antibiotic or intermediate from the culture, and (iii) when an intermediate is produced in step (i), converting said intermediate into said antibiotic.

2. The method of claim 1, wherein the bacterium is a wild-type *Deinococcus bacterium*.

3. The method of claim 1, wherein the bacterium is a recombinant *Deinococcus bacterium*.

4. The method of claim 1, wherein the bacterium is cultured in a defined medium.

5. The method of claim 1, wherein the bacterium is cultured in a complex medium.

6. The method of claim 1, wherein the bacterium is cultured at a pH comprised between 4 and 8.

7. The method of claim 1, wherein the bacterium is cultured in a fermentation device or as a continuous culture.

8. The method of claim 1, wherein the antibiotic is chemically modified after collection or purification.

* * * * *